United States Patent [19]

James

[11] Patent Number: 4,645,456
[45] Date of Patent: Feb. 24, 1987

[54] ADHESIVE COMPOSITIONS FOR TOOTH ENAMEL

[75] Inventor: Jack L. James, Long Beach, Calif.

[73] Assignee: Lee Pharmaceuticals, Inc., South El Monte, Calif.

[21] Appl. No.: 769,481

[22] Filed: Aug. 26, 1985

[51] Int. Cl.$^4$ .............................................. A61K 6/02
[52] U.S. Cl. ............................. 433/217.1; 433/228.1; 523/118; 523/116
[58] Field of Search ............... 523/116, 115, 117, 118; 433/217.1, 228.1

[56] References Cited

U.S. PATENT DOCUMENTS 4,380,432  4/1983  Orlowski et al. ................... 523/118
4,525,493  6/1985  Omura et al. ....................... 523/116

*Primary Examiner*—Lorenzo B. Hayes
*Attorney, Agent, or Firm*—Joseph E. Mueth

[57] ABSTRACT

The novel system for the bonding of dental filling composites and orthodontic adhesives to tooth enamel wherein the enamel is treated with a 2.5%–15% aqueous solution of a strong mineral acid or organic acid. The enamel is rinsed with water and thoroughly dried. A curable hydrophilic monomer primer is placed upon the enamel, said enamel primer being selected from the group consisting of esters having the generic formula:

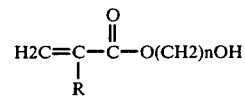

wherein R is H or $CH_3$ and n is 1–8; esters of the general formula:

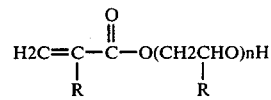

wherein R=H or $CH_3$ and n is 2–8;
the mono and dimethacrylates or acrylates of glycerol; and
acrylic or methacrylic acid.

A methacrylate or acrylate based orthodontic adhesive or dental composite is cured on the surface of the primed enamel to give a material strongly bonded to the enamel surface.

12 Claims, No Drawings

ADHESIVE COMPOSITIONS FOR TOOTH ENAMEL

DESCRIPTION OF THE PRIOR ART

In dentistry and orthodontics there is a great need to strongly and reliably bond polymeric systems to the enamel portions of teeth. Dimethacrylate and monomethacrylate based composites and adhesives are presently used to bond to the surface of tooth enamel. Presently, prior to placement of methacrylate composites and adhesives on the surface of tooth enamel, etching with a highly acidic solution is required. Typically, a 35-50% aqueous solution of orthophosphoric acid is applied to tooth enamel for 1-2 minutes. This process creates deep pits and irregularities in the enamel surface so that mechanical interlocking of the methacrylate resins and enamel occurs. Deeply etching the enamel for bonding work creates adequate adhesion. It also creates some problems.

In the prior art, the enamel etched with the highly acidic solution is demineralized and the demineralized zones are then filled with methacrylic resin that cures in place. Occasionally, when orthodontic work is removed an unsightly demineralized white spot remains and is quite persistent. The cured resin in the demineralized zone prevents remineralization and the layer of etched enamel/cured resin must be simply allowed to wear away. A system that eliminates the need for etching would eliminate this problem.

The etching agent must be allowed to sit on each tooth for 1-2 minutes and costs the dentist time. Dentists are very time oriented and a system that eliminated or shortened the etching step would be valuable to them.

The deep etch filled with cured resin makes clean up of the cured resin difficult after the removal of orthodontic work. Also, cured orthodontic resin that has penetrated into the deep pits of highly etched enamel will frequently pull portions of the enamel away when being removed. This causes damage to the tooth and is undesirable. A bonding system that did not utilize a deep etch would eliminate the destruction of enamel.

There have been a few attempts to overcome the problem of strong acid etching in bonding composites and orthodontic adhesives to tooth enamel. There have been technical papers published in the dental journals describing systems where crystals of calcium phosphate are grown upon the surface of teeth from an aqueous solution which provides an irregular surface to which conventional orthodontic adhesives may bond utilizing mechanical interlocking as the primary means of retention. L. D. Caulk Company of Milford Del. has marketed an orthodontic adhesives system based upon crystal growth on the enamel surface. However, this approach has not met with great success. It is believed that by the use of a less vigorous acid wash followed by application of a different enamel primer which is hydrophilic and curable, the art of bonding dental filling composites and orthodontic adhesives to tooth enamel has been substantially improved. Accordingly, it is to be anticipated that this invention will be widely adopted by those skilled in the art.

SUMMARY OF THE INVENTION

Briefly, the present invention comprises a system whereby methacrylate and acrylate based dental adhesives and restoratives are bonded to tooth enamel by first cleansing the enamel with a 2-15% by weight aqueous solution of a strong inorganic or organic acid, preferably having a pKa of less than 3 for a period of 10-30 seconds; followed by rinsing, drying, and application of a curable hydrophilic monomer primer of the general formula below is placed upon the enamel:

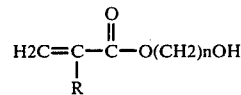

where
R=H or CH$_3$
n=1-8;
monomer of the formula:

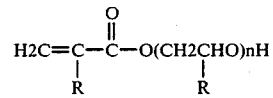

where
R=H or CH$_3$
n=2-8;
the mono and di methacrylates or acrylates of glycerol; and acrylic or methacrylic acid.

A methacrylate or acrylate based orothodontic adhesive or dental composite is cured on the surface of the primed enamel to give a material strongly bonded to the enamel surface.

It is an object of this invention to provide a novel system for the bonding of dental filling composites and orthodontic adhesives to tooth enamel.

It is an object of this invention to overcome the problems of bonding methacrylate and acrylate based composites and adhesives to tooth enamel without deeply etching the enamel of the teeth.

It is an object of this invention to provide a novel enamel primer system.

These and other objects and advantages of this invention will be apparent from the detailed description which follows.

As was mentioned in a description of the prior art, teeth are normally etched with a 35-50% by weight solution of a strong mineral or organic acid for a period of 60-120 seconds. Usually, orthophosphoric acid is the acid used. Other acids may include but is not limited to hydrochloric acid, nitric acid, citric acid, acetic acid, trichloroacetic acid, pyruvic acid, nitrous acid, or hydrobromic acid. In the novel process disclosed in this document, the teeth are preferably treated with a 2-15% acid solution for 10-30 seconds. The use of the less vigorous conditions according to this invention eliminates the majority of damage to the tooth enamel. The enamel is not nearly so deeply etched as with previous treatments. The treatment with the weaker acid solution for the shorter period of time allows the tooth enamel to be cleaned without highly etching the surface.

Enamel in the oral environment is covered with layers of water and organic matter. The organic matter is composed of proteins, bacteria, and food residue which are deposited on the tooth from saliva. Washing the enamel with a dilute acid solution removes the organic matter from the tooth leaving a surface more suitable for bonding.

The enamel is rinsed clean of the acid wash and dried with clean, dry compressed air or a solvent that carries away water in an azetrope. Such a solvent is acetone.

At this point, the surface of the enamel is clean of organic contaminants and the bulk of the water has been removed. The surface of the enamel is still covered with adsorbed water. A conventional dental composite or adhesive is quite hydrophobic and will not effectively bond to the wet surface. Also, conventional methacrylate and acrylate based orthodontic and dental adhesives hydrolyze upon the wet enamel surface yielding hydrolysis products that lower the surface energy of the enamel and prevent the adhesive from wetting the enamel surface. Low adhesion is the result.

In the novel process for bonding to tooth enamel, a low viscosity hydrophilic methacrylic or acrylic ester containing a hydroxyl is brushed onto the surface of the enamel. The hydrophilic monomer can penetrate and bond with the water adsorbed onto the surface of the enamel and intimate contact between enamel and monomer can thusly be attained. The methacrylate and acrylate based monomers used in the novel bonding process hydrolyze on the wet enamel surface to yield products that do not poison the enamel surface as is the case with conventional dental adhesives and composites. In the novel bonding procedure, the hydrophilic hydroxyl containing monomer may be of the general formula:

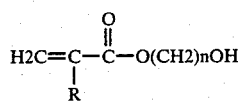

where
R=H or CH3
n=1-8
Also monomers of the formula:

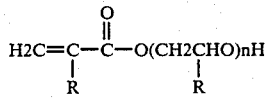

where
R=H or CH3
n=2-8
Also the mono and dimethacrylates or acrylates of glycerol are monomers that can penetrate adsorbed water and bond to enamel and function as enamel primer. Acrylic and methacrylic acid are also useful.

After priming the surface of the cleansed enamel with the hydrophilic monomer a conventional dental composite or adhesive may be cured in place to provide a strong bond to the tooth enamel.

DESCRIPTION OF THE PREFERRED EMBODIMENTS

A perferred formula for the mildly acidic solution to clean the surface of the enamel is as follows:

| ----- % by weight |
|---|
| 95.0% water |
| 5.0% orthophosphoric acid |
| 100% Total |

The preferred monomers for use in priming the cleansed enamel surface are 2-hydroxy ethyl methacrylate, 3-hydroxy propyl methacrylate, 1,3-glycerol dimethacrylate and 1,3-glycerol diacrylate. Various additives may be placed in the primers such as peroxides, ultraviolet light stabilizers, tertiary amines, thickeners and polymerization inhibitors.

EXAMPLE #1

Orthodontic Adhesive

Extracted human molars were prophied with a slurry of dental pumice in water using rubber cup and dental handpiece. This practice is common among orthodontists in preparing teeth for orthodontic work. The prophied teeth were rinsed with water and dried with tissue paper. A solution of 5% orthophosphoric acid in water was applied to the teeth with a cotton pellet and allowed to stand for 15 seconds. The teeth were rinsed thoroughly with distilled water and blown clear of moisture with clean, dry compressed air. A.C.S. reagent grade acetone was applied to the teeth with a clean cotton pellet and allowed to evaporate away.

Equal proportions of a solution of 1.0% (by weight) dibenzoylperoxide in 2-hydroxy ethyl methacrylate and a solution of 3.5% (by weight) N,N di(2-hydroxy ethyl)para toluidine in 2-hydroxy ethyl methacrylate was mixed and quickly brushed onto the surface of the tooth enamel in a thin layer. Excess amounts of the mixture were dabbed away with a tissue to leave a slightly moistened surface. A mixture of equal proportions of part A paste and part B paste from a commercially available orthodontic adhesive was applied to the bases of orthodontic brackets (Lee Pharmaceutical's Metal Mesh, 0.022 inch straight slot, flat base) which were then quickly seated on the primed tooth enamel before the orthodontic paste had an opportunity to cure. The commercially available orthodontic paste used was part A & B paste of Lee Pharmaceutical's Prestige Orthodontic Bonding System (Catalog #2079-100). The teeth were stored in water at 37 degrees centigrade for 24 hours and the tensile force required to rupture the bond between the bonded bracket and the enamel was measured using a model TTC Instron Corporation universal testing machine. The average force required to rupture the bonds was 740 pounds per square inch. The adhesive strength of the bonds is more than adequate for orthodontic work and compares favorably to that obtained with conventional orthodontic bracket adhesives utilizing a full conventional etch.

The adhesive residue from the ruptured adhesion samples was removed from the tooth enamel using standard orthodontic scaling instruments. The scaled enamel cleaned up easily leaving a surface that was visually indistinguishable from that of virgin enamel. Examination of the scaled enamel under scanning electron microscope showed the enamel to be clean of adhesive residue and undamaged aside from the minor scratching associated with scaling off the adhesive residue. The novel orthodontic bonding system allows for brackets to be bonded to enamel surface without significantly damaging the enamel or creating asthetic problems.

EXAMPLE #2

Orthodontic Adhesive

"No-Mix Type"

Extracted human molars were prophied with a slurry of dental pumice in water using rubber cup and dental handpiece. This practice is common among orthodontists in preparing teeth for orthodontic work. The prophied teeth were rinsed with water and dried with tissue paper. A solution of 5% orthophosphoric acid in water was applied to the teeth with a cotton pellet and allowed to stand for 15 seconds. The teeth were rinsed thoroughly with distilled water and blown clear of moisture with clean, dry compressed air. A.C.S. reagent grade acetone was applied to the teeth with a clean cotton pellet and allowed to evaporate away.

Enamel Primer Composition

A solution of 3.5% N,N di(2-hydroxy ethyl)para toluidine in 2-hydroxy ethyl methacrylate was brushed upon the enamel surfaces in a thin layer.

A thin coating of the following composition was brushed onto the base of orthodontic brackets identical to those used in Example 1:

| Bracket Primer Composition % by weight | |
|---|---|
| 63.0 | diethylene glycol dimethacrylate |
| 26.8 | ethoxylated disphenol A dimethacrylate |
| 6.7 | polymethylmethacrylate |
| 3.5 | N,N di(2-hydroxy ethyl) para toluidine |
| 100% | Total |

A thin coating of an adhesive paste was placed on the base of the primed brackets. The adhesive paste had the following composition:

| Adhesive Paste Composition % by weight | |
|---|---|
| 63.4% | Bis phenol A diglycidyl ether dimethacrylate (Bis/GMA) |
| 21.1% | diethylene glycol dimethacrylate |
| 11.5% | pyrogenic silica 0.04 micron average particle size |
| 4.0% | dibenzoyl peroxide |
| 100% | Total |

The coated brackets were quickely seated on the primed enamel surface and allowed to polymerize. The samples were then placed in water at 37 degrees centigrate and the tensile bond strength was measured as in Example #1. The average tensile bond strength obtained was 600 pounds per square inch. The bond strength is quite adequate for orthodontic work. As in Example #1 the enamel surfaces were easily scaled of adhesive residue leaving a clean, undamaged enamel surface.

EXAMPLE #3

Use of Various Types of Acid

A variety of acids are useful for preparing the cleansing solution that is applied to the teeth prior to application of the methacrylate or acrylate based adhesives or restorative composites. In order to demonstrate this fact, the procedure in Example #2 of this patent was repeated substituting a number of different acids in place of the orthophosphoric acid used in 5% by weight aqueous cleansing solution. The acids used were nitric acid, hydrochloric acid, acetic acid, citric acid, and pyruvic acid. The results from the substitution of these acids for orthophosphoric acid in Example #2 can be seen in the table below.

| Acid (5% by weight in water Pretreatment | Adhesion (PSI) |
|---|---|
| nitric acid | 640 PSI |
| hydrochloric acid | 790 PSI |
| citric acid | 525 PSI |
| pyruvic acid | 440 PSI |
| acetic acid | 300 PSI |
| no acid (control) | 0 PSI (too weak to test) |

EXAMPLE #4

Bonding a Restorative Composite

The novel system for bonding to enamel may also be used to bond restorative dental composites to enamel as well as orthodontic adhesives.

Extracted human molars were prophied with a slurry of dental pumice in water using rubber cup and dental handpiece. This practice is common among dentists in preparing teeth for bonding. The prophied teeth were rinsed with water and dried with tissue paper. A solution of 5% orthophosphoric acid in water was applied to the teeth with a cotton pellet and allowed to stand for 15 seconds. The teeth were rinsed thoroughly with distilled water and blown clear of moisture with clean, dry compressed air. A.C.S. reagent grade acetone was applied to the teeth with a clean cotton pellet and allowed to evaporate away.

Equal proportions of a solution of 1.0% (by weight) dibenzoylperoxide in 2-hydroxy ethyl methacrylate and a solution of 3.5% (by weight) N,N di(2-hydroxy ethyl)para toluidine in 2-hydroxy ethyl methacrylate was mixed and quickly brushed onto the surface of the tooth enamel in a thin layer. Excess amounts of the mixture were dabbed away with a tissue to leave a slightly moistened surface.

Restodent (Lee Pharmaceuticals, South El Monte, Calif.), a commercially available restorative composite was mixed per the manufacturer's instructions and applied to the base of orthodontic brackets (identical to those used in Examples 1 and 2). The brackets were firmly seated on the enamel surface and the restorative material was allowed to cure. The samples were stored in water at 37 degrees centigrate for 24 hours and then tested for tensile bond strength on the Instron testing machine. Orthodontic brackets were bonded to the teeth since they allowed a convenient method of measuring the adhesion of the Restodent restorative composite. The average tensile bond strength obtained was 720 pounds per square inch.

Having fully described the invention, it is intended that it be limited solely by the lawful scope of the appended claims.

What is claimed is:

1. A method of bonding methacrylate and acrylate based dental adhesives and restoratives to tooth enamel which comprises first cleansing the enamel with an about 2-15% by weight aqueous solution of a strong inorganic or organic acid; followed by rinsing, drying, and application to the tooth enamel of a curable hydrophilic monomer primer consisting essentially of a member selected from the group consisting of:

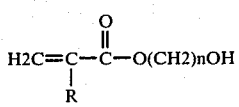

where
R=H or CH$_3$
n=1-8;
monomers of the formula:

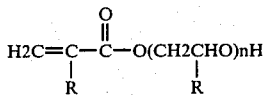

where
R=H or CH$_3$
n=2-8;
the mono and di methacrylates or acrylates of glycerol; and acrylic or methacrylic acid.

2. The method of claim 1 wherein the strong inorganic or organic acid has a pKa of less than 3 and it is applied for a period of 10 to 30 seconds.

3. The method of claim 1 wherein a polymerizable methacrylate or acrylate based dental adhesive or composite is subsequently cured in place on the primed enamel to give a highly bonded material.

4. The method of claim 1 whereby the acid used is orthophosphoric acid.

5. The method of claim 1 whereby the acidic solution is 5% by weight aqueous orthophosphoric acid.

6. The method of claim 1 whereby the monomer enamel primer applied to the tooth enamel is 2-hydroxyethylmethacrylate.

7. The method of claim 1 whereby the monomer enamel primer applied to the tooth enamel is 3-hydroxypropylmethacrylate.

8. The method of claim 1 whereby the monomer enamel primer applied to the tooth enamel is 2-hydroxy ethylmethacrylate or 3-hydroxypropyl methacrylate containing a tertiary amine.

9. The method of claim 1 whereby the monomer enamel primer applied to the tooth enamel is 2-hydroxy ethylmethacrylate or 3-hydroxypropyl methacrylate containing a peroxide useful as a polymerization initiator.

10. The method of claim 1 whereby the monomer enamel primer is 2-hydroxy ethyl methacrylate or 3-hydroxy propyl methacrylate containing a tertiary amine which is mixed with the same monomer containing a peroxide and brushed onto the acid treated tooth enamel prior to polymerization.

11. The method of claim 1 wherein the monomer enamel primer is a mono or dimethacrylate or acrylate of glycerol.

12. The method of claim 1 wherein the monomer enamel primer is acrylic or methacrylic acid.

* * * * *